US009694192B2

(12) United States Patent
Vansickle et al.

(10) Patent No.: US 9,694,192 B2
(45) Date of Patent: *Jul. 4, 2017

(54) IMPLANTABLE MEDICAL DEVICE WITH A PRIMARY AND RECHARGEABLE BATTERY

(71) Applicant: Boston Scientific Neuromodulation Corporation, Valenica, CA (US)

(72) Inventors: Dennis Allen Vansickle, Lancaster, CA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 57 days.

This patent is subject to a terminal disclaimer.

(21) Appl. No.: 14/502,570

(22) Filed: Sep. 30, 2014

(65) Prior Publication Data

US 2015/0100108 A1     Apr. 9, 2015

Related U.S. Application Data

(60) Provisional application No. 61/887,231, filed on Oct. 4, 2013.

(51) Int. Cl.
*A61N 1/36* (2006.01)
*A61N 1/378* (2006.01)
(Continued)

(52) U.S. Cl.
CPC ....... *A61N 1/3787* (2013.01); *A61N 1/36125* (2013.01); *A61N 1/378* (2013.01); *A61N 1/36071* (2013.01); *A61N 1/37276* (2013.01)

(58) Field of Classification Search
CPC ... A61N 1/36125; A61N 1/378; A61N 1/3787
(Continued)

(56) References Cited

U.S. PATENT DOCUMENTS 4,096,866 A    6/1978  Fischell
4,408,607 A   10/1983  Maurer
(Continued)

FOREIGN PATENT DOCUMENTS

CN    101612451 A    12/2009
JP    06-125994       5/1994
(Continued)

OTHER PUBLICATIONS

International Search Report and Written Opinion regarding corresponding PCT Application No. PCT/US2014/058540, dated Dec. 19, 2014.

*Primary Examiner* — William Levicky
(74) *Attorney, Agent, or Firm* — Lewis, Reese & Nesmith, PLLC

(57) ABSTRACT

An implantable medical device (IMD) having a rechargeable and primary battery is disclosed, as are algorithms for automatically selecting use of these batteries at particular times. In one IMD embodiment, the primary battery acts as the main battery, and an algorithm allows the IMD to draw power from the primary battery until its voltage reaches a threshold, after which the algorithm allows the IMD to draw power from the rechargeable battery when it is sufficiently charged. In another IMD embodiment, the rechargeable battery acts as the main battery, and an algorithm allows the IMD to draw power from the rechargeable battery if it is sufficiently charged; otherwise, the algorithm allows the IMD to draw power from the primary battery. Further disclosed are techniques for telemetering data relevant to both batteries to an external device, and for allowing a patient to choose use of a particular one of the batteries.

20 Claims, 13 Drawing Sheets

(51) Int. Cl.
*H02J 7/00* (2006.01)
*H02J 9/00* (2006.01)
*A61N 1/372* (2006.01)

(58) Field of Classification Search
USPC .................. 320/103, 128; 307/44–46, 64–66
See application file for complete search history.

(56) References Cited

U.S. PATENT DOCUMENTS

| | | |
|---|---|---|
| 4,548,209 A | 10/1985 | Wielders et al. |
| 4,556,061 A | 12/1985 | Barreras et al. |
| 4,793,353 A | 12/1988 | Borkan |
| 5,080,096 A | 1/1992 | Hooper et al. |
| 5,222,494 A | 6/1993 | Baker, Jr. |
| 5,235,979 A | 8/1993 | Adams |
| 5,312,439 A | 5/1994 | Loeb |
| 5,314,458 A | 5/1994 | Najafi et al. |
| 5,391,193 A | 2/1995 | Thompson |
| 5,591,212 A | 1/1997 | Keimel |
| 5,650,974 A | 7/1997 | Yoshimura |
| 5,733,313 A | 3/1998 | Barreras et al. |
| 5,769,877 A | 6/1998 | Barreras |
| 5,957,956 A * | 9/1999 | Kroll .................... A61N 1/375 607/5 |
| 6,164,284 A | 12/2000 | Schulman et al. |
| 6,185,452 B1 | 2/2001 | Schulman et al. |
| 6,208,894 B1 | 3/2001 | Schulman et al. |
| 6,272,382 B1 | 8/2001 | Faltys et al. |
| 6,308,101 B1 | 10/2001 | Faltys et al. |
| 6,381,496 B1 | 4/2002 | Meadows et al. |
| 6,553,263 B1 | 4/2003 | Meadows et al. |
| 6,650,942 B2 | 11/2003 | Howard et al. |
| 6,920,359 B2 | 7/2005 | Meadows et al. |
| 7,079,893 B2 | 7/2006 | Greatbatch et al. |
| 7,177,698 B2 | 2/2007 | Klosterman et al. |
| 7,209,784 B2 | 4/2007 | Schmidt |
| 7,337,001 B2 | 2/2008 | Schmidt |
| 7,428,438 B2 | 9/2008 | Parramon et al. |
| 7,437,193 B2 | 10/2008 | Parramon et al. |
| 7,545,398 B2 | 6/2009 | Sawada |
| 7,657,315 B2 | 2/2010 | Schmidt |
| 7,737,581 B2 | 6/2010 | Spurlin et al. |
| 7,801,600 B1 | 9/2010 | Carbunaru |
| 7,801,615 B2 | 9/2010 | Meadows et al. |
| 7,822,480 B2 | 10/2010 | Park et al. |
| 7,840,279 B2 | 11/2010 | He |
| 7,977,911 B2 * | 7/2011 | Maireanu ............... H02M 3/156 307/66 |
| 8,027,728 B2 | 9/2011 | Schmidt et al. |
| 8,175,717 B2 | 5/2012 | Haller et al. |
| 8,185,212 B2 | 5/2012 | Carbunaru et al. |
| 8,386,048 B2 | 2/2013 | McClure et al. |
| 8,401,659 B2 | 3/2013 | Von Arx et al. |
| 8,478,404 B2 | 7/2013 | Maile et al. |
| 2007/0150019 A1 * | 6/2007 | Youker ................ A61N 1/3787 607/29 |
| 2008/0300660 A1 | 12/2008 | John |

FOREIGN PATENT DOCUMENTS

| | | |
|---|---|---|
| JP | 2000122811 | 4/2000 |
| JP | 2001-322515 | 11/2001 |
| JP | 2002201321 | 7/2002 |
| WO | 2012/116407 A1 | 9/2012 |
| WO | 2013/078092 A1 | 5/2013 |

* cited by examiner

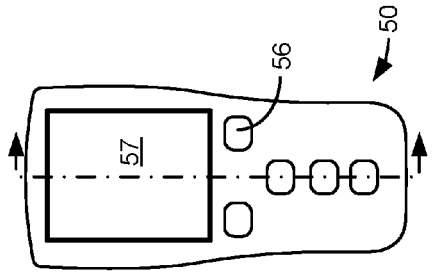
*Figure 2D (prior art)*
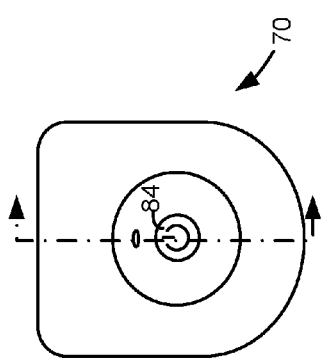
*Figure 2C (prior art)*
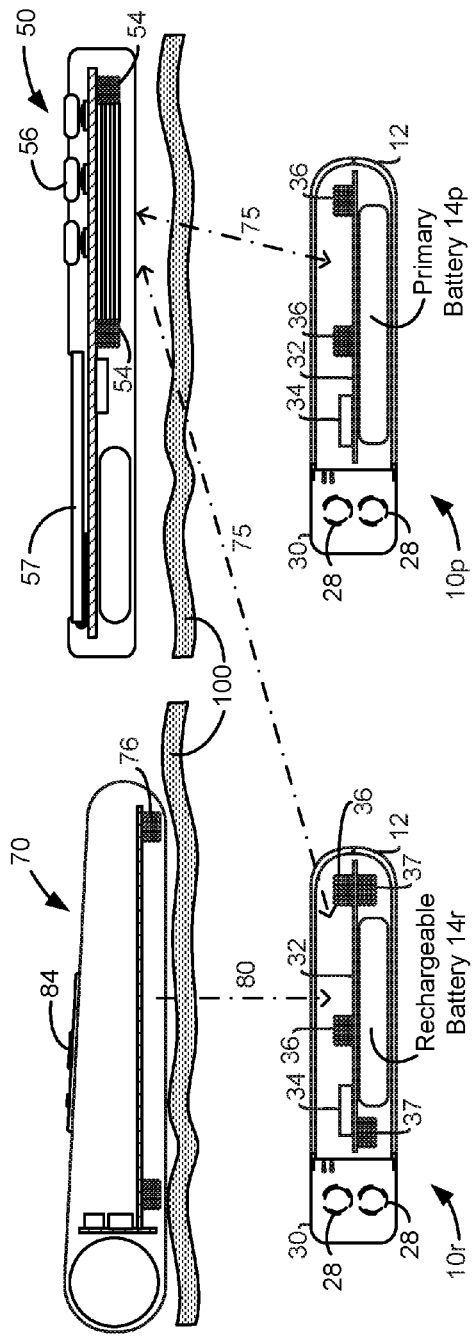
*Figure 2B (prior art)*
*Figure 2A (prior art)*

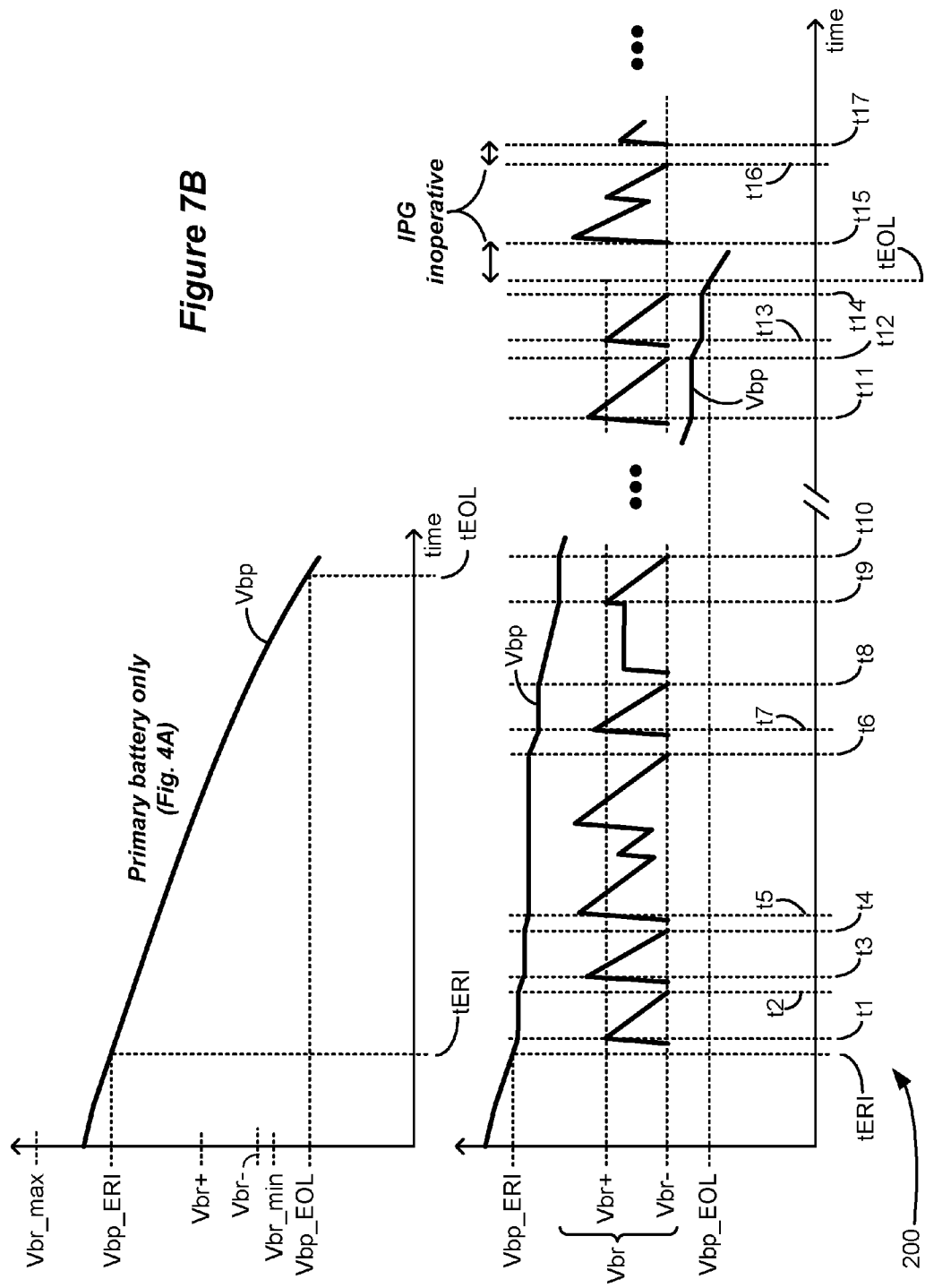

IMPLANTABLE MEDICAL DEVICE WITH A PRIMARY AND RECHARGEABLE BATTERY

CROSS REFERENCE TO RELATED APPLICATIONS

This is a non-provisional of U.S. Provisional Patent Application Ser. No. 61/887,231, filed Oct. 4, 2013, which is incorporated herein by reference in its entirety, and to which priority is claimed.

FIELD OF THE INVENTION

The present invention relates to implantable medical device systems, and in particular to systems involving implantable stimulators.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIG. 1, an SCS system typically includes an Implantable Pulse Generator (IPG) 10, which includes a biocompatible device case 12 formed of a conductive material such as titanium for example. The case 12 typically holds the circuitry and battery necessary for the IPG to function, as described in detail below. The IPG 10 is coupled to distal electrodes 16 designed to contact a patient's tissue. The distal electrodes 16 are coupled to the IPG 10 via one or more electrode leads (two such leads 18 and 20 are shown), such that the electrodes 16 form an electrode array 22. The electrodes 16 are carried on a flexible body 24, which also houses the individual signal wires 26 coupled to each electrode. In the illustrated embodiment, there are eight electrodes on lead 18, labeled E1-E8, and eight electrodes on lead 20, labeled E9-E16, although the number of leads and electrodes is application specific and therefore can vary. The leads 18, 20 contain proximal electrode contacts 29, which couple to the IPG 10 using lead connectors 28 fixed in a non-conductive header material 30 such as an epoxy.

As shown in the cross-sections of FIGS. 2A and 2B, an IPG 10 typically includes a printed circuit board (PCB) 32 to which various electronic components 34 are mounted, some of which are discussed below. A telemetry (antenna) coil 36 is used to transmit/receive data to/from an external controller 50, as explained further below. In these examples, the telemetry coil 36 is within the case 12, although it can also be placed in the header 30 in other examples. U.S. Pat. No. 8,577,474 discloses telemetry antennas in both of these locations, and is incorporated herein by reference.

IPGs can differ in the type of battery employed. FIG. 2A shows an IPG 10r that contains a rechargeable battery 14r (where "r" denotes "rechargeable"). To facilitate charging of battery 14r, the IPG 10r contains an additional charging coil 37, which wirelessly receives a magnetic charging field 80 from a coil 76 in a hand-holdable and portable external charger 70 (FIG. 2C). Such means of charging battery 14r using an external charger 70 occurs transcutaneously through the patient's tissue 100 via magnetic induction. When the external charger 70 is turned on (switch 84), and referring to FIG. 3A, charging circuitry 94 generates an AC current (Icharge) in coil 76. This produces an AC magnetic charging field 80 (e.g., of 80 kHz), which induces an AC current in charging coil 37 in the IPG 10r. This current is rectified 44 to a DC level used to recharge the battery 14r, perhaps via battery charging and protection circuitry 46. Rechargeable batteries 14r can be formed using different chemistries, but lithium ion polymer batteries are popular for use in implantable medical devices, and can be charged to a battery voltage (Vbr) of about Vbr_max=4.2 Volts (see FIG. 4A) in one example.

IPGs with rechargeable batteries 14r can transmit data to their associated external chargers 70 using Load Shift Keying (LSK), which involves using serial bits to be telemetered (from LSK modulator 40) to modulate the impedance of charging coil 37 (via transistor 42). This manifests as a change in the voltage used by the external charger 70 to produce the AC current (Icharge) in coil 76, and so such voltage can be demodulated 96 and the data bits recovered for interpretation for the external charger 70's control circuitry 92. LSK telemetry is well known, and further details concerning LSK telemetry are disclosed in U.S. Patent Application Ser. No. 61/877,877, filed Sep. 13, 2013, which is incorporated herein by reference.

FIG. 2B shows an IPG 10p that contains a non-rechargeable primary battery 14p (where "p" denotes "primary"). Unlike a rechargeable battery 14r, the electrochemical reaction in a primary battery 14p is not reversible by passing a charging current therethrough. Instead, a primary battery 14p will eventually expend the materials in one or both of its electrodes, and thus has a limited life span. Once the battery 14p is exhausted, it will be necessary to explant IPG 10p from the patient so that the battery 14p can be replaced and the IPG 10p re-implanted, or (more likely) so that a new IPG 10p with a fresh battery 14p can be implanted. Primary batteries 14b can be formed using different chemistries, but Lithium CFx batteries, or Lithium/CFx-SVO (Silver Vanadium Oxide) hybrid batteries are popular for use in implantable medical devices, and produce battery voltages of Vbp_max=1.2-3.2 Volts (see FIG. 4B) for example. Because battery 14p is not rechargeable, there is no need for a charging coil (compare 37 in FIG. 2A) in IPG 10p, and no need for an external charger 70. Structures relevant to charging that would not be used with a primary battery IPG 10p are shown in dotted lines in FIG. 3A.

Regardless whether a rechargeable or primary battery 14r or 14p is used in the IPG 10, that battery ultimately provides the power (Vbr, Vbp) for the bulk of the operative circuits 47 in the IPG 10 via power supply node Vdd, such as analog or digital circuits and their associated regulators. Analog circuits 47 can comprise thermistors, band gap voltage references, oscillators and clocks, modulation 41 and demodulation 43 circuitry (FIG. 3A), analog measurement and routing circuitry, etc. Digital circuits 47 can include the control circuitry 38 and other digital logic circuits, including memory circuits. Other operative circuits 49 in the IPG may be powered directly and only by Vbr or Vbp, as shown in FIG. 3B, such as a resonant tank circuit including telemetry coil (antenna) 36, which tank is coupled to modulation 41 and demodulation 43 circuitry; and a DC-DC converter that generates a power supply V+ for the current generation circuitry (DAC) that produces the stimulation currents at the electrodes 16, as shown in FIG. 3B. FIG. 3B is largely taken from U.S. patent application Ser. No. 13/966,510, filed Aug. 14, 2013, and is incorporated herein by reference. However, operative circuits 47 and 49 can also both be powered by power supply node Vdd.

Control circuitry 38 can comprise a microcontroller integrated circuit, such as MSP430, manufactured by Texas Instruments, which is described in data sheets at that company's website, or as described in U.S. Patent Application Publication 2012/0095529, the latter of which is incorporated herein by reference. Control circuitry 38 may also comprise a microprocessor integrated circuit, a collection of integrated circuits, a collection of non-integrated circuits, or a collection of both integrated and non-integrated circuits— essentially any hardware capable of operating the IPG in the manners disclosed herein.

Various circuits 45 may intervene between Vbr or Vbp provided by batteries 14r or 14p and power supply node Vdd, such as one or more switches used to disconnect the battery in case of a undervoltage or overcurrent condition. See U.S. Patent Application Publication 2013/0023943, which is incorporated herein by reference. Circuits 45 may also include regulators, boost (buck) or step-up (step down) converters, or other conditioning circuits to provide to power supply node Vdd a stable voltage of appropriate magnitude for IPG 10 power supply use.

FIG. 2D shows the external controller 50, such as a hand-held portable patient controller or a clinician's programmer, for communicating with either of IPG 10r or IPG 10p. The external controller 50 typically comprises a graphical user interface similar to that used for a portable computer, cell phone, or other hand held electronic device, including touchable buttons 56 and a display 57, which may also be touch sensitive to allow for patient input. The external controller 50 is used to set or adjust the therapy settings the IPG 10 will provide to the patient, such as which electrodes 16 are active, whether such electrodes sink and source current, and the duration, frequency, and amplitude of pulses formed at the electrodes. The external controller 50 can also act as a receiver of data from the IPG 10, such as various data reporting on the IPG's status, the level of the IPG 10's battery 14r or 14p, and other parameters measured or logged at the IPG 10.

Such communications can occur transcutaneously and bi-directionally via link 75 between a telemetry coil 54 in the external controller 50 and the telemetry coil 36 in the IPG 10, either of which can act as the transmitter or the receiver. Referring to FIG. 3A, when a series of digital data bits is to be sent from the external controller 50 to the IPG 10, control circuitry 60 in the external controller 50 (e.g., a microcontroller) provides these bits in sequence to a modulator 61. Modulator 61 energizes coil 54 with an alternating current (AC) whose frequency is modulated in accordance with the state of the data bit currently being transferred—what is known as a Frequency Shift Keying (FSK) protocol. For example, the coil 54 may nominally be tuned to resonate at 125 kHz in accordance with the inductance of the coil 54 and a tuning capacitor (not shown), with data states '0' and '1' altering this center frequency to f0=121 kHz and f1=129 kHz respectively. The frequency-modulated current through the coil 54 in turn generates a frequency-modulated magnetic field comprising link 75, which in turn induces a frequency-modulated current in the IPG's telemetry coil 36. This received signal is demodulated 43 back into the series of digital data bits, and sent to control circuitry 38 (e.g., a microcontroller) in the IPG 10 for interpretation. Data telemetry in the opposite direction from IPG 10 to external controller 50 via link 75 occurs similarly via modulator 41 and demodulator 62.

Other means for communicating between an external controller and an IPG are known as well, including RF communications such as Bluetooth, Bluetooth Low Energy, Wifi, NFC, Zigbee, etc., that are enabled by patch, wire, or slot antennas. In this instance, link 75 would comprise a longer-range electromagnetic field, rather than a near-field magnetic field enabled by coils 54 and 36. An external controller may comprise a dedicated IPG communication device, or a multi-functional mobile device such as a cell phone, a tablet computer, or another hand-holdable portable control device, as disclosed in U.S. Patent Application Ser. No. 61/874,863, filed Sep. 6, 2013. Optical means of communication may also be used between the external controller and the IPG. See the above-incorporated '877 Application.

Whether an IPG 10r with a rechargeable battery 14r or an IPG 10p with a primary battery 14p is warranted for a given patient depends on weighing several pros and cons associated with each. An IPG with a rechargeable battery can be charged when needed without the need of explantation, but can be more costly, as a charging coil in the IPG and an external charger are required. The need to recharge the rechargeable battery can also be a hassle for a patient. If a patient is missing his external charger, and referring to FIG. 4A, there is a risk that the rechargeable battery may deplete to a voltage (i.e., Vbr=Vbr_min; e.g., 2.0V) insufficient to power the IPG, thus depriving the patient of stimulation therapy. If the voltage of the rechargeable battery becomes lower still and is deeply depleted (i.e., Vbr=Vbr_dd), the patient may be unable to recharge the rechargeable battery with his external charger, and may need to visit a clinician to recover the IPG to a working state. Rechargeable batteries may also suffer from reliability concerns, as they can wear out and work less efficiently as they are cycled over their lifetimes, which can increase the likelihood that a patient will be deprived of therapy. If the rechargeable battery is significantly worn and can no longer hold an adequate charge, there is a possibility that explantation and re-implantation of a fresh IPG will be required.

An IPG with a primary battery does not suffer from these same concerns; for example, there is no additional cost or hassle associated with charging. However, a primary battery IPG will eventually require explantation and re-implantation of a fresh IPG as the primary battery depletes. A curve showing primary battery depletion as a function of time is shown in FIG. 4B, and two significant points are noted. First in time is that corresponding to the issuance of an Elective Replacement Indicator (ERI). ERI issues when the primary battery has sufficiently depleted (i.e., to Vbp_ERI), and will soon reach its End Of Life (EOL). As the primary battery continues to deplete, it will eventually reach EOL, which like Vbr_min described earlier comprises a battery voltage Vbp_EOL insufficient to power the IPG, and at which time therapy will cease.

ERI, when issued, is typically stored at the IPG, and can cause a speaker in the IPG to "beep" to alert the patient that this threshold has been crossed. ERI can also be queried upon a visit to the patient's clinician's office using special wireless monitoring tools, or via telephonic monitoring. ERI is a significant event in the life of a primary battery IPG, as it indicates that the IPG is nearing its EOL and must soon be explanted and replaced. Manufacturers of primary battery IPGs typically design ERI to issue a predetermined time before EOL is reached, such as 2-6 months, to allow a patient sufficient time to schedule necessary replacement surgery. However, the time period between ERI and EOL is not always reliable, and a patient may not be able to schedule surgery quickly enough to have his primary battery IPG replaced before its EOL is reached. Again, this raises the concern that a patient with a primary battery IPG will be deprived therapy.

The inventors are concerned about the possibility that either the primary battery IPG or the rechargeable battery IPG can leave a patient without needed therapy when its battery is sufficiently depleted, and provide solutions to mitigate these concerns.

BRIEF DESCRIPTION OF THE DRAWINGS

FIGS. 2A and 2B respectively show a rechargeable battery IPG and a primary battery IPG, in accordance with the prior art.

FIGS. 2C and 2D respectively show an external charger for a rechargeable battery IPG and an external controller for either the rechargeable battery IPG or the primary battery IPG, in accordance with the prior art.

FIG. 7B shows the voltages of the rechargeable and primary batteries using the algorithm of FIG. 7A.

DETAILED DESCRIPTION

An implantable medical device (IMD) such as an Implantable Pulse Generator (IPG) having a rechargeable battery and a primary battery is disclosed, as are battery selection algorithms for automatically selecting either of these batteries for use at particular times. In one IPG embodiment, the primary battery acts as the main battery, and an associated algorithm allows the IPG to draw power from the primary battery until its voltage reaches a threshold (e.g., Vbp=Vbp_ERI), after which the algorithm allows the IPG to draw power from the back-up rechargeable battery when it is sufficiently charged. In another IPG embodiment, the rechargeable battery acts as the main battery, and an associated algorithm allows the IPG to draw power from the rechargeable battery if it is sufficiently charged; otherwise, the algorithm allows the IPG to draw power from the back-up primary battery. Providing a back-up battery in the improved IPG is particularly useful to extend the life of the IPG, and/or to reduce circumstances in which a patient would be deprived of IPG therapy because its main battery has been depleted. Further disclosed are techniques for telemetering and reviewing data relevant to both batteries at an external device, and for allowing a patient to choose use of a particular one of the batteries in the IPG from the external device.

Figure 5:
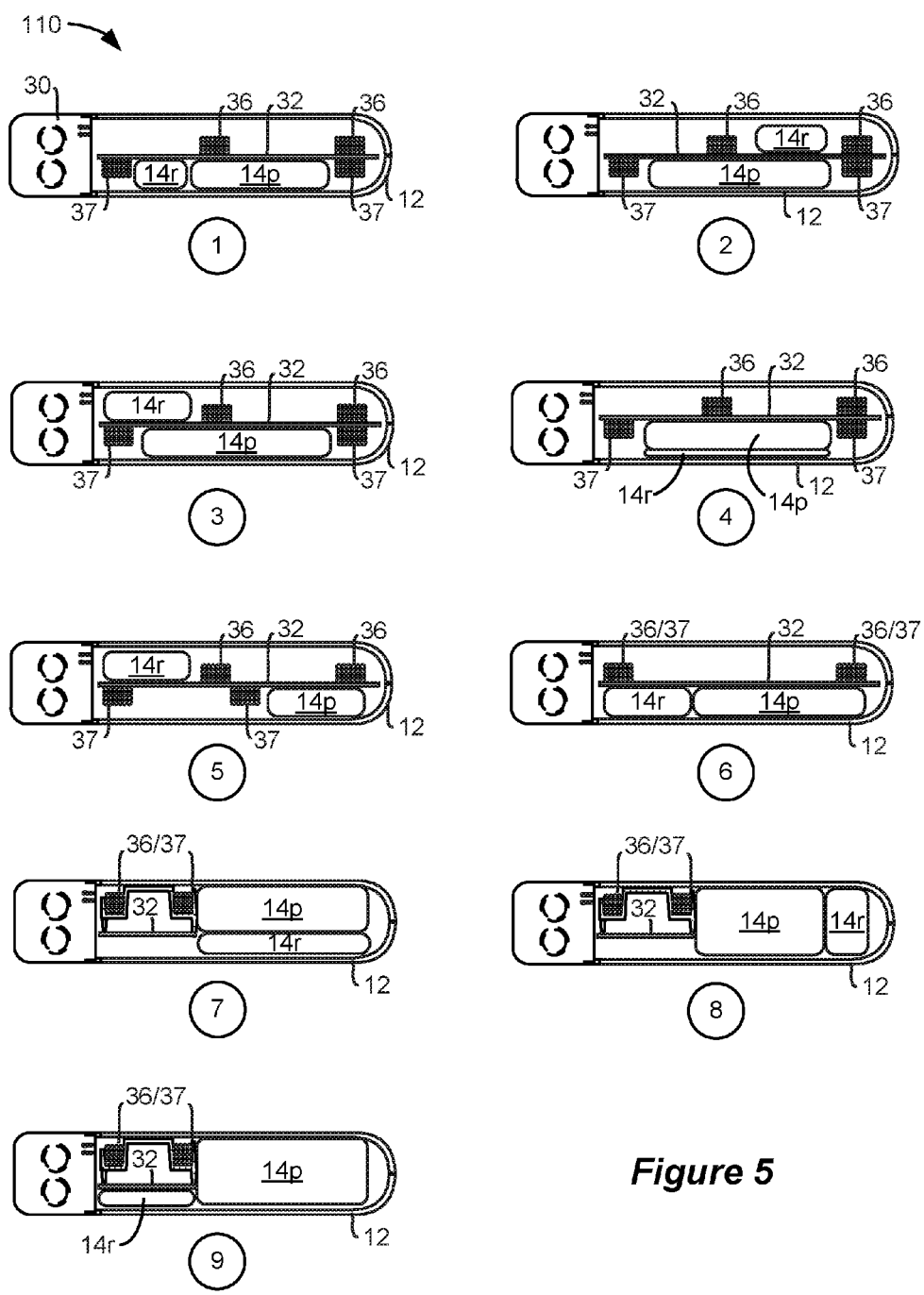
FIG. 5 shows various examples of an improved dual-battery IPG having both a rechargeable battery and a primary battery.

Various examples of the improved dual-battery IPG 110 are shown in FIG. 5. In each case, the IPG 110 contains both a rechargeable battery 14r and a primary battery 14p. The batteries 14r and 14p can be located anywhere inside the IPG 110 so long as they don't impact other IPG functions or interfere unduly with telemetry. Shown are examples in which the batteries 14p and 14r are side-by-side on one side of the IPG's PCB 32 (1, 6); on opposite sides of the PCB (2, 3, 5); inside the IPG's telemetry coil (2); outside of the IPG's charging coil 37 (5); stacked on one side of the PCB (4); to the side of the PCB (7, 8, 9); side-by-side to the side of the PCB (8); stacked to the side of the PCB (7); and on one side of the PCB and to the side of the PCB (9). Examples 7-9 are based on the IPG design disclosed in U.S. Patent Application Ser. No. 61/874,194, filed Sep. 5, 2013, which is incorporated herein by reference.

In all of the examples, the IPG 110 includes a charging coil 37 for receiving operational power from an external charger 70 (FIG. 2C) and for allowing recharging of the rechargeable battery 14r. Each also includes a telemetry coil 36 for communicating with an external controller 50 (FIG. 2D), although other forms of antennas could be used for this purpose, as explained earlier. Telemetry antennas or coils 36 could also be placed in the IPG's header 30 instead of within its case 12, as also explained earlier. In examples 6-9, a single coil 36/37 is provided for performing both telemetry and charging functions, with these functions being (for example) time multiplexed at the single coil.

In most of the examples shown in FIG. 5, the primary battery 14p is larger than the rechargeable battery 14r. This is in recognition of a first IPG embodiment, described later with respect to FIGS. 7A-7B, in which the primary battery 14p is preferentially used as the main battery for the IPG 110, with the rechargeable battery 14r instead being used as a back-up battery when the voltage of the primary battery becomes too low. As such, the primary battery 14p is as large as possible, while the rechargeable battery 14r may be relatively small. However, this is not strictly necessary, and in a second embodiment, described later with respect to FIGS. 8A-8B, the rechargeable battery 14r is preferentially used as the main battery for the IPG 110, with the primary battery 14p being used as a back-up battery when the rechargeable battery is not sufficiently charged. In this embodiment, the rechargeable battery 14r might be as large as possible and may comprise the larger batteries depicted in FIG. 5, while the primary battery 14p is relatively small and may comprise the smaller depicted batteries.

However, it should be noted that which battery 14r or 14p is considered the main battery in the IPG 110 is not necessarily determined on its size: given differences in their chemistries, one of these batteries 14r or 14p may be more powerful than the other, but may still be smaller. Moreover, it is not necessary to consider either battery 14r or 14p as the main battery in the IPG 110, and either of the battery-use algorithms disclosed below, or even other battery use algorithms, can be used with any dual-battery IPG 110.

FIG. 5 merely illustrates some examples of IPG 110, and the batteries 14r and 14p can be placed anywhere in the IPG 110 as its design permits, and various combination of the depicted examples could also be used. If necessary to have relatively large batteries 14r and 14p, a larger IPG case 12 could be used for the IPG 110. More than one rechargeable battery 14r, and/or more than one primary battery 14b, could also be used, although not depicted.

Figure 6A:
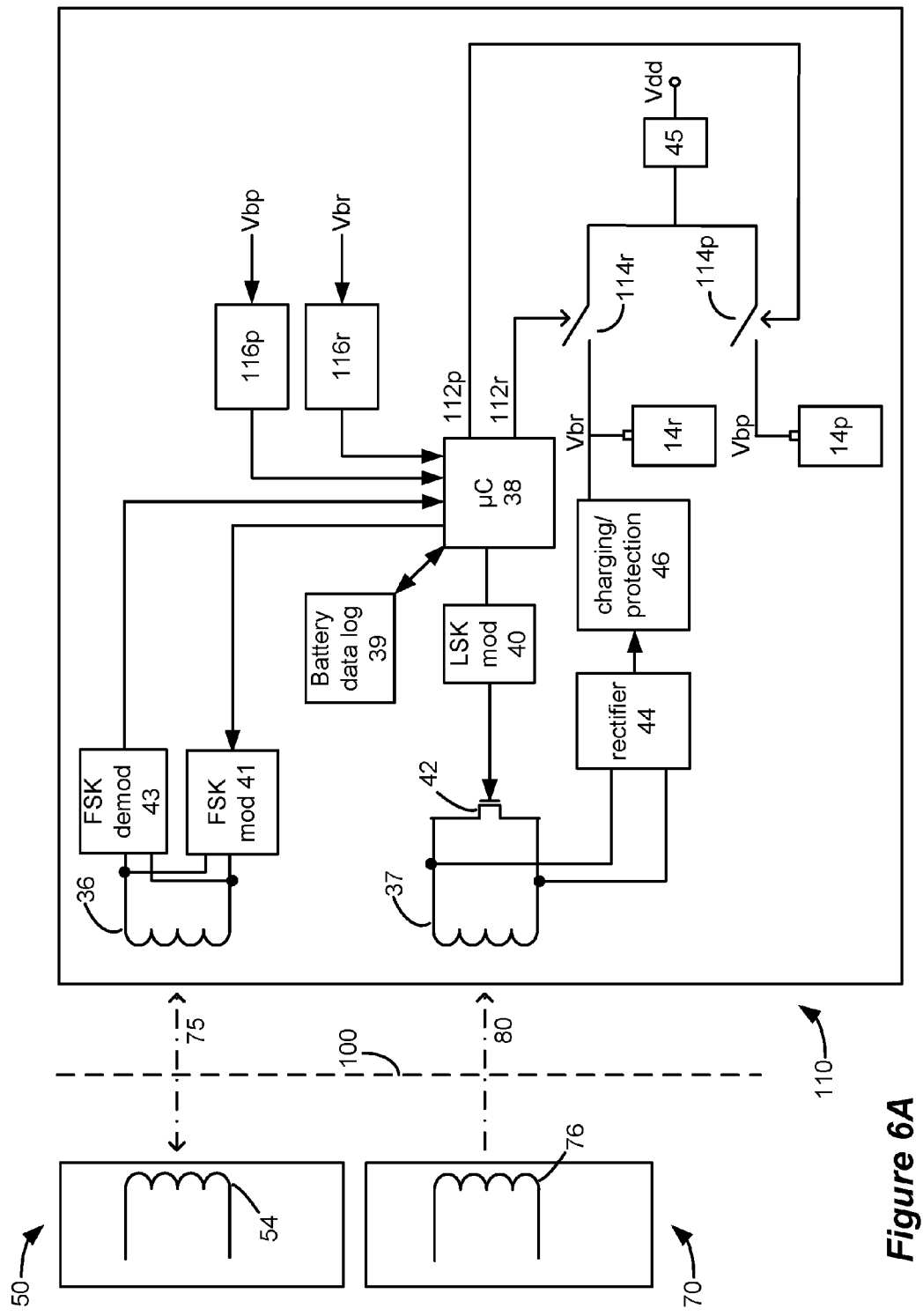
FIG. 6A shows circuitry within the improved dual-battery IPG, including switches to allow either the primary and rechargeable battery to be used to provide power to the IPG.

FIG. 6A shows the circuitry in the IPG 110, much of which was explained earlier with respect to FIGS. 3A and 3B, and which will therefore not be repeated. New to the circuitry are the inclusion of both the rechargeable battery 14r and the primary battery 14p, as well as switches 114r and 114p which allow either of these batteries to be connected to the operative circuitry in the IPG 110 (at power supply node Vdd). Switches 114r and 114p are controlled respectively by control signals 112r and 112p. Also provided are battery voltage measuring circuits 116r and 116p for measuring the values of the voltages of batteries 14r and 14p, i.e., Vbr and Vbp, and for reporting them to the IPG's control circuitry 38, which in turn issues appropriate control signals 112r and 112p to select either of the batteries 14r or 14p for use. In a preferred embodiment, and as explained further below, only one of control signals 112r or 112p is asserted at any given time to connect only one of batteries 14r or 14p to the power supply node Vdd, although this is not strictly necessary. A battery data log 39 is also associated with the control circuitry 38, and may comprise a portion of the control circuitry's memory.

Figure 6B:
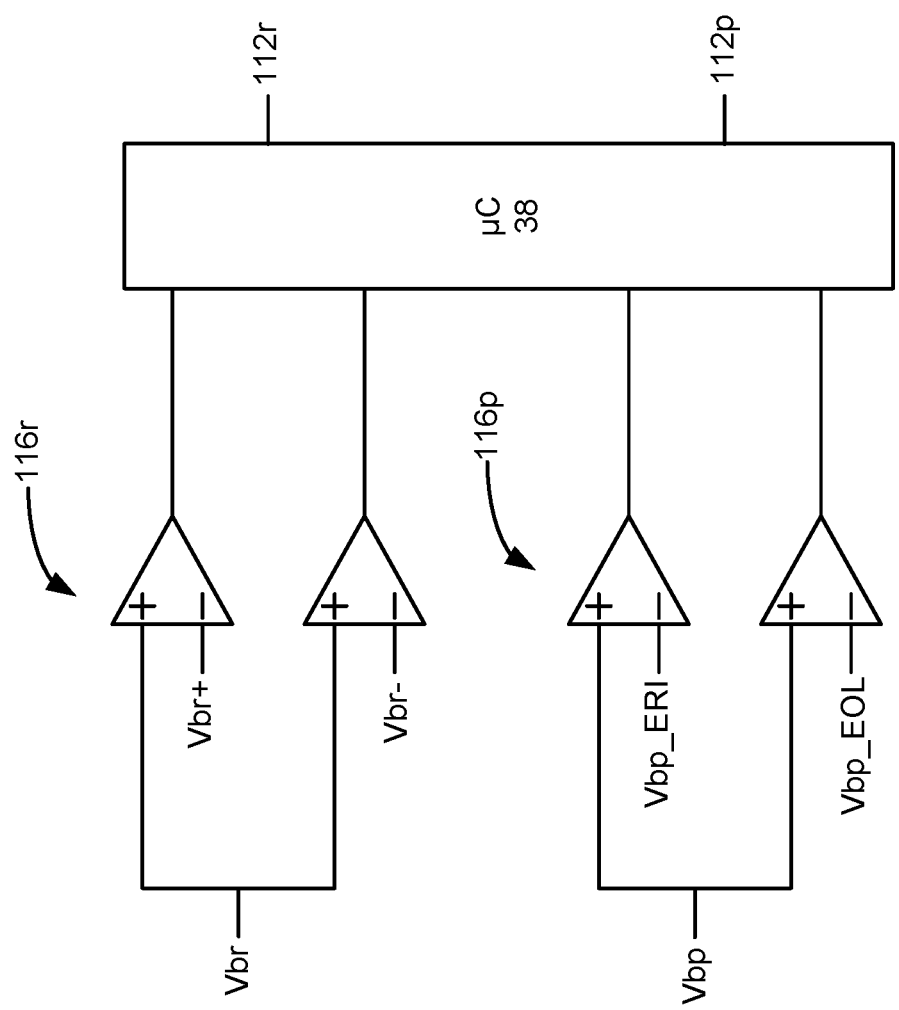
FIG. 6B shows battery voltage measuring circuitry for the rechargeable and primary batteries in the improved IPG.

Battery voltage measuring circuits 116r and 116p could be implemented in several different ways. For example, they could comprise Analog-to-Digital (A/D) converters, although if the control circuitry 38 includes A/D inputs able to interpret analog battery voltages, this would not be required. Measuring circuits 116r and 116p could also comprise operational or differential amplifiers. In the example shown in FIG. 6B, the measuring circuits 116r and 116p are implemented with comparators to digitally inform the control circuitry 38 of the values of the batteries voltages Vbr and Vbp relative to certain voltage thresholds (e.g., Vbr+, Vbr−, Vbp_ERI, Vbp_EOL) whose relevance are explained further below. These thresholds may be generated using well-known bandgap voltage generators circuits for example (not shown), and may be programmable and adjustable, for example by telemetering new values from the external controller 50 (FIG. 2D) and storing them for control circuitry 38 access. Alternatively, the control circuitry 38 can be programmed to implement in logic the functionality of the measuring circuits of FIG. 6B.

Figure 7A:
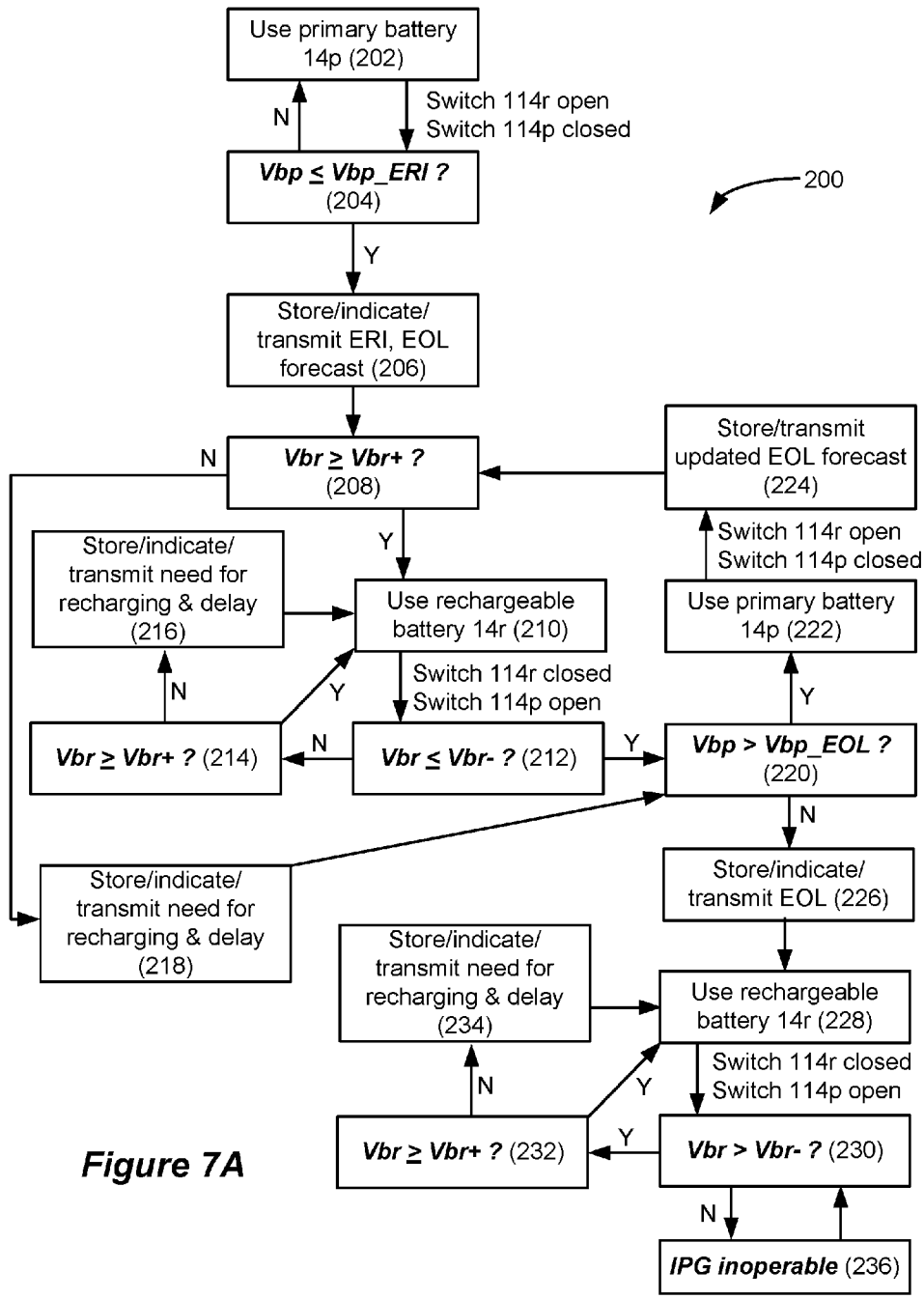
FIG. 7A shows an algorithm preferably useable with a dual-battery IPG having a main primary battery, which algorithm automatically selects use of the primary battery or the rechargeable battery.

IPG 110 can use either battery 14r or 14p for its operational power, and in different embodiments either battery can be considered as the main battery from which the IPG 110 will preferentially draw its operating power. FIG. 7A shows an algorithm 200 for an IPG 110 in which the primary battery 14p acts as the main battery until its battery voltage Vbp depletes to a threshold voltage (e.g., Vbp=Vbp_ERI), and thereafter uses the back-up rechargeable battery 14r when possible. One skilled will realize that algorithm 200 can be implemented by programming the IPG's control circuitry 38 to perform the steps of the algorithm using inputs from battery voltage measuring circuits 116r and 116p to issue control signals 112r and 112p accordingly.

Using Vbp_ERI—the voltage at which the Elective Replacement Indicator (ERI) would normal issue for a primary battery IPG as explained earlier—as the threshold at which the rechargeable battery 14r is potentially used in algorithm 200 is not strictly necessary, and other threshold voltages could be used, leaving ERI to operate as before. However, use of Vbp_ERI is preferred because it informs as to when the primary battery 14p will soon be expended, and thus informs when recharging and use of the back-up rechargeable battery 14r may become important to the patient.

Figure 9:
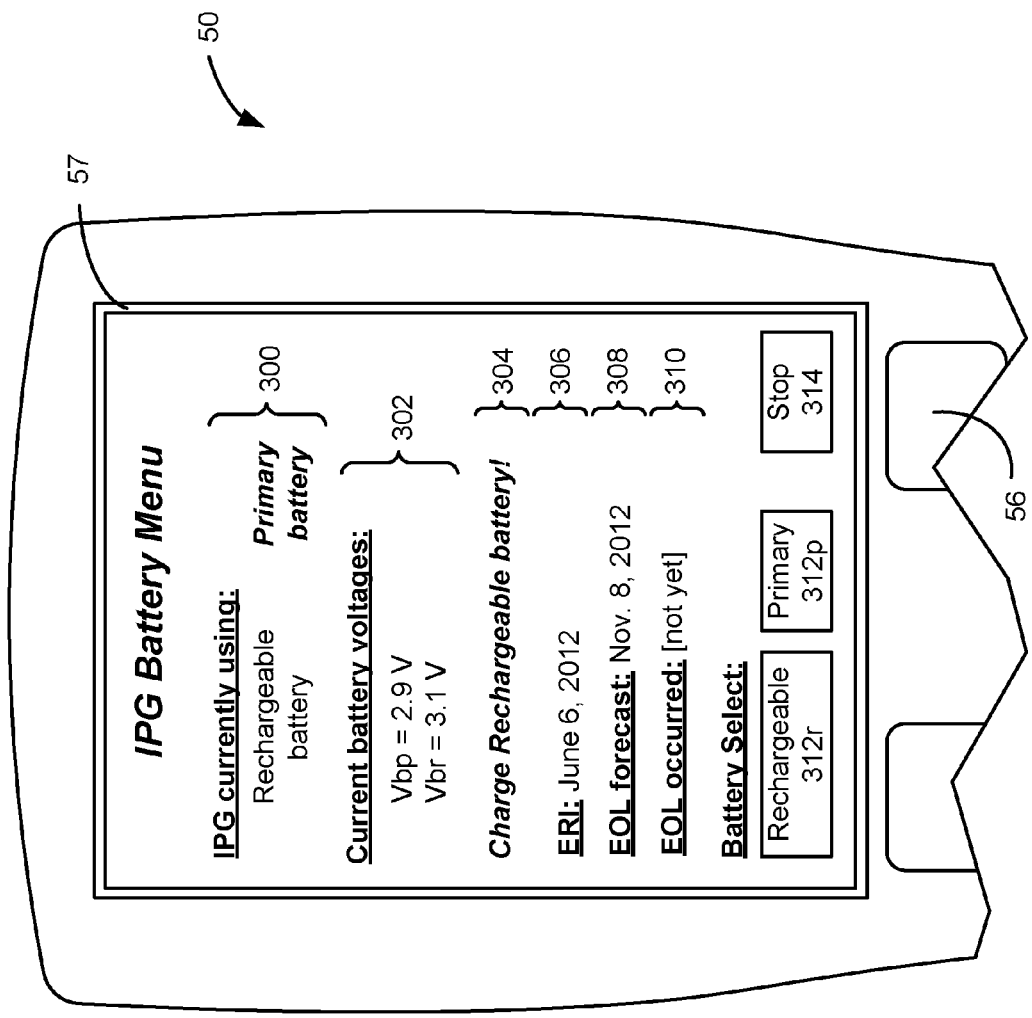
FIG. 9 shows a graphical user interface of an external device for communicating with the improved dual-battery IPG.

As shown in FIG. 7A, algorithm 200 initially uses the primary battery 14p to power the IPG 110 (202), and so switch 114p is closed to connect the primary battery 14p to IPG power supply node Vdd (e.g., 112p='1') while switch 114r is opened to disconnect the rechargeable battery 14r (e.g., 112r='0'). The primary battery 14p is assessed during its use using voltage battery measuring circuit 116p to determine when it has depleted to Vbp≥Vbp_ERI (204), i.e., whether ERI has issued, which may occur after many years of use of the IPG 110. If ERI has issued, an indication of ERI is stored in the IPG 110, indicated to the patient, and/or transmitted to an external device of a patient (206), as discussed further with reference to FIG. 9 below. Storage of ERI can occur in battery data log 39 (FIG. 6A), which is preferably time stamped to record when ERI issued; such stored ERI information may also be accessible by a patient's clinician. ERI can be indicated to the patient, such as by "beeping" of the IPG 110, as described earlier. Additionally, in accordance with another aspect of the invention, the ERI indication is preferably telemetered to an external device of the patient for review (FIG. 9). Algorithm 200 may also similarly store and transmit to the patient a forecasted EOL, which at least initially may comprise a set time from the issuance of the ERI (e.g., 2-6 months).

The algorithm 200 can then assess whether the rechargeable battery 14r is sufficiently charged for use, i.e., if Vbr≥Vbr+ (208), using voltage battery measuring circuit 116r. As shown in the top graph of FIG. 7B, this threshold Vbr+ is above the minimum voltage (Vbr_min) at which the rechargeable battery 14r can operate the IPG 110, but may also be below the maximum voltage for the rechargeable battery 14r (Vbr_max). In other words, Vbr+ preferably comprises a suitable level of charge to make use of the rechargeable battery 14r worthwhile: it doesn't need to be fully charged, but it is preferably sufficiently charged to power the IPG 110 for a meaningful time. For example, if Vbr_max=4.2V and Vbr_min=2.0V, Vbr+ might be set to 2.7V. Again, the particular value for threshold Vbr+ can vary. In other examples, it can comprise any value over Vbr_min, or can comprise Vbr_max.

If Vbr≥Vbr+ (208), the algorithm 200 can then use the rechargeable battery 14r by closing switch 114r (e.g., 112r='1'), and can disconnect the primary battery at switch 114r (e.g., 112p='0') (210). This can be seen in the bottom graph in FIG. 7B: before time t1, the patient starts charging rechargeable battery 14r, and Vbr begins to rise. (Values for Vbr lower than threshold Vbr− are not shown). When Vbr≥Vbr+ at time t1, the rechargeable battery 14r is used (210). Vbr thus begins to fall after t1 as the rechargeable battery 14r is drawn upon, and Vbp stays constant as it is now disconnected and is not being drawn upon.

If the rechargeable battery 14r is used (210) and it is not recharged, Vbr will eventually fall to a lower threshold V≤Vbr− (212). As shown in the top graph of FIG. 7B, this threshold Vbr− is preferably set just above the minimum voltage (Vbr_min) at which the rechargeable battery 14r can operate the IPG 110. For example, if Vbr_min=2.0V, Vbr− might be set to 2.2V. Setting Vbr− slightly above Vbr_min provides a guardband to ensure that rechargeable battery 14r will be able to operate the IPG 110 when selected. Again, the particular value for threshold Vbr− can vary, and could comprise Vbr_min.

Assuming Vbr has not yet fallen to Vbr− (212), Vbr can be assessed to determine if it is still ≥Vbr+ (214). If so, use of the rechargeable battery 14r continues (210). If Vbr eventually falls below Vbr+ (214), algorithm 200 preferably stores, indicates to the patient, and transmits for patient review an indication of the need for recharging using external charger 70 (216). Again, this can implicate battery data log 39 (FIG. 6A), in which a binary indication of the need for charging can be stored, or which can also store the current value of Vbr for the rechargeable battery 14r from which the need for recharging can be inferred. Indication of the need for recharging could again include a "beep" from the IPG 110 distinguishable from that use for ERI. Transmission of the need for recharging can again implicate an external device of the patient (FIG. 9). The algorithm 200 may also delay at this step 216 for a sensible time interval (e.g., 1 minute) so that battery assessment and potential battery switching does not occur needlessly quickly. Nonetheless, while the rechargeable battery 14r may need recharging (216), its use still continues (210), as it has not yet reached Vbr− (212).

If Vbr<Vbr+ at earlier step (208) after ERI was reached, algorithm 200 preferably stores, indicates, and transmits an indication of the need for recharging, and delays (218), similar to what occurred at step 216. Note that although the algorithm 200 would prefer to use the rechargeable battery 14r at this point (218), operational power for the IPG 110 is still being drawn from the primary battery 14p.

After step 218 (which resulted from desire but inability to use the rechargeable battery 14r), of if Vbr falls to Vbr≥Vbr− (212) (which resulted from use of the rechargeable battery 14r, which is now expended; see time t2 in FIG. 7B), the primary battery 14p is used (or continues to be used) if possible. It is useful to determine at this point whether the primary battery 14r has reached its End Of Life (EOL) (220). This can occur by assessing whether the primary battery voltage Vbp>Vbp_EOL, or by the algorithm 200 determining in some other fashion that the primary battery 14p is not able to power the IPG 110 for any number of reasons.

If Vbp>Vbp_EOL (220), the switches 114r and 114p are configured to connect and use (or continue to use) the primary battery 14p (222), and to disconnect the rechargeable battery (if necessary). Additionally, it may be useful to update the forecasted EOL, and to store it (in battery data log 39) and/or transmit it to the patient (224). Such updating of the forecasted EOL for the primary battery 14p can occur in several different manners. In a simple example, the control circuitry 38 can keep track of how long the rechargeable battery 14r had been used in its last session (e.g., between times t1 and t2), and add this time to the EOL forecast as stored in battery data log 39 for example. Referring again to FIG. 7B, when Vbr=Vbr− at time t2 and the primary battery 14p is used (222), Vbp will start to fall as it is drawn upon.

At this point, algorithm returns to step 208. If the patient has sufficiently recharged the rechargeable battery 14r (Vbr≥Vbr+) (208), it is again used until it is depleted (212-216). If the patient hasn't sufficiently recharged the rechargeable battery 14r (Vbr<Vbr+) (208), use of the primary battery continues (218-224).

Examples of this process are shown further in FIG. 7B. At time t3, the patient has sufficiently charged the rechargeable battery 14r to Vbr+ (208), and indeed has even continued to charge it beyond that threshold. (Indeed, the patient would preferably always charge rechargeable battery 14r to Vbr_max if possible). Rechargeable battery 14r is thus used (210) until it reaches Vbr=Vbr− at t4 (212), after which the primary battery 14p is used (222). At time t5, the patient again charges rechargeable battery 14r to a level sufficient for its use (208), and further charges the battery 14r twice before Vbr falls to Vbr− at time t6, thus allowing use of the rechargeable battery 14r (210) continuously during this time period. At time t8, Vbr equals Vbr−(212), and the primary battery 14p is once again used and drawn upon (222). Thereafter, the patient has again started to charge rechargeable battery 14r, and so Vbr increases, but not sufficiently to Vbr+ (208). The primary battery 14p thus continues to be used (222) and Vbp continues to fall (and Vbr stays constant at its insufficiently-charged level) until t9 when the rechargeable battery 14r is again sufficiently charged (208) and used (210).

This process continues until such time as the primary battery 14p can no longer be used, i.e., when Vbp≤Vbp_EOL (220). At this point, the EOL indication can be stored, indicated, and transmitted (226), similar to what occurred earlier for the ERI and need for recharging indications. Only the rechargeable battery 14r can thereafter be used to provide operating power to the IPG 110 (228), and switches 114r and 114p are configured to permanently select the rechargeable battery 14r. As such, the IPG 110 will now only operate if the rechargeable battery 14r can power the IPG. In this regard, the rechargeable battery 14r is preferably used if it has any charge sufficient to operate the IPG 110, i.e., if Vbr>Vbr− (230). Alternatively, the Vbr threshold for use of the rechargeable battery 14r at step 230 could comprise a higher threshold, such as Vbr+ (see step 208), or perhaps even Vbr_max, to ensure that the IPG 110 can be powered by the rechargeable battery 14r for a meaningful time. But given the non-functionality of the primary battery 14p, it is preferred to use the rechargeable battery if it is at all capable of operating the IPG 110, even if not significantly charged.

The algorithm 200 can continue to assess the need for recharging (232) and can undertake recharging actions if necessary (234), similar to steps 214 and 216 earlier. If Vbr≤Vbr− (230), the IPG 110 cannot operate (236), and the patient will be deprived of IPG therapy until the rechargeable battery 14r is charged again (230, 228).

FIG. 7B illustrates advantages to the use of rechargeable battery 14r as the back-up to primary battery 14b in IPG 110 when algorithm 200 is employed. By recharging and use of the rechargeable battery 14r after ERI issues, the time to EOL for the primary battery 14p is extended, allowing the patient to use his IPG 110 much longer when compared to use of a primary battery 14p alone, as comparison of the graphs in FIG. 7B shows. This is due to the fact that the primary battery 14p is not drawn upon, and Vbp thus remains constant, while the rechargeable battery 14r is being used. Moreover, by recharging and using the rechargeable battery 14r, the patient can continue to use their IPG 110 even after the EOL is reached for the primary battery 14p, making scheduling of explantation surgery less exigent. In short, the likelihood of deprivation of patient therapy is reduced through use of algorithm 200 and dual-battery IPG 110.

Figure 8A:
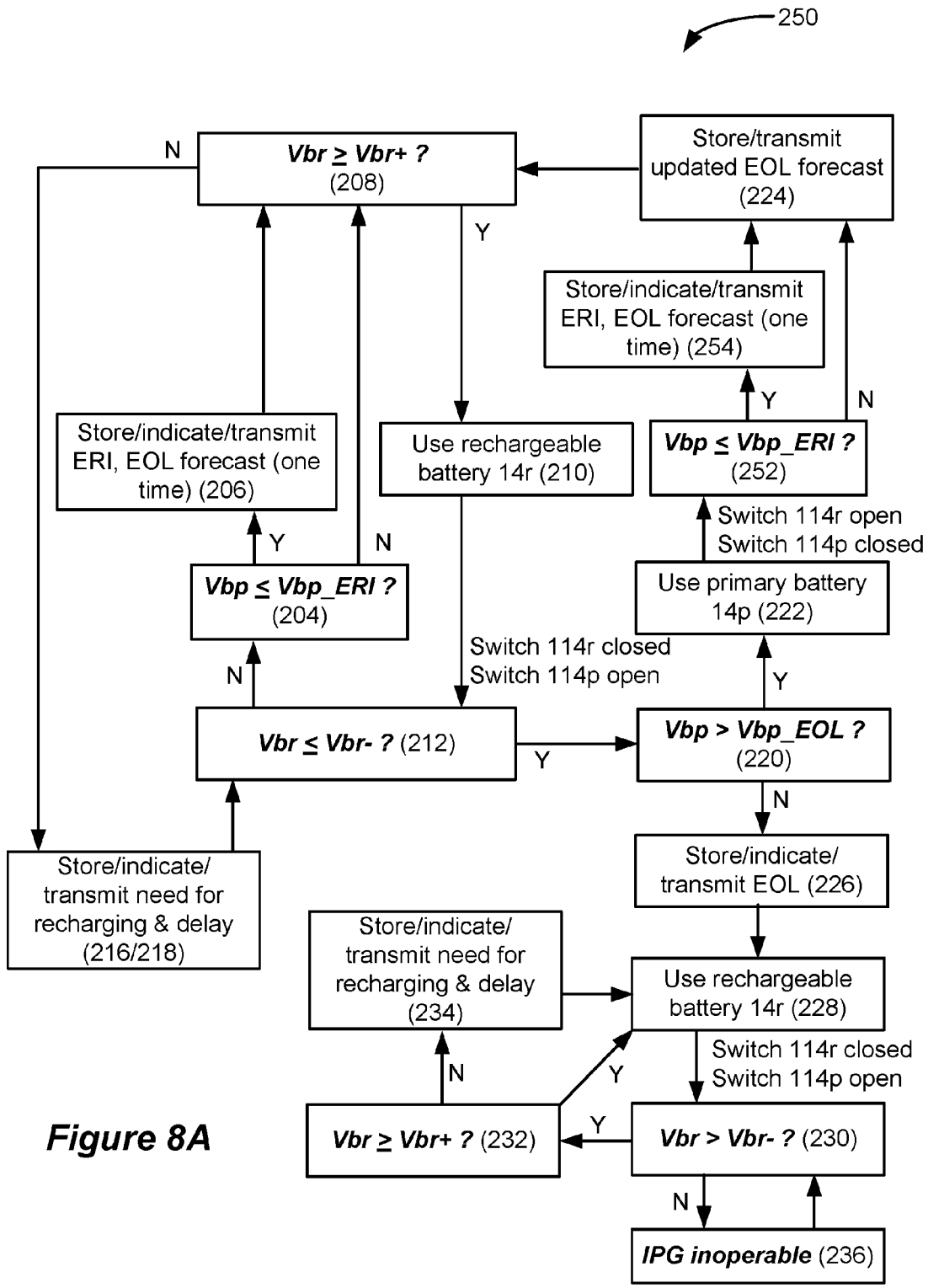
FIG. 8A shows an algorithm preferably useable with a dual-battery IPG having a main rechargeable battery, which algorithm automatically selects use of the primary battery or the rechargeable battery.

FIG. 8A shows an algorithm 250 in which the rechargeable battery 14r acts as the main battery in the IPG 110 and is used when suitably charged, but where primary battery 14p is otherwise used to prevent deprivation of patient therapy. Many of the same voltage thresholds used in algorithm 200 (Vbr+, Vbr−, Vbp_ERI, Vbp_EOL) can be used in algorithm 250 as well, and their relevance is thus not repeated. Many of the same steps used in algorithm 250 can also be used, although perhaps in different orders, and thus the same elements numerals are used for some of the steps.

Algorithm 250 initially uses the rechargeable battery 14r to power the IPG 110 (210), and switches 114p and 114r are set accordingly. If one assumes that Vbr=Vbr_max initially, the rechargeable battery voltage would be Vbr>Vbr− (212), at which point the algorithm can assess whether ERI has issued for the primary battery 14p, i.e., Vbp≤Vbp_ERI (204), and if so, ERI and a forecasted EOL can be stored, indicated, and transmitted to the patient (206). As ERI only issues once during the life of a primary battery 14p, these ERI actions likewise preferably only occur once in algorithm 250, and occurs at this point to ensure that ERI is recognized even if the rechargeable battery 14r is being used. However, it should be noted that assessment and use of ERI with algorithm 250 is optional, as it is assumed that IPG 110 is this instance mainly powered by the rechargeable battery 14a, and that back-up primary battery 14p may be of less importance. Indeed, in an IPG 110 so configured, it may not be necessary to explant the IPG 110 once the primary battery 14p has depleted (to EOL), as the rechargeable battery 14r can still be used to power the IPG 110 in conventional fashion (see, e.g., IPG 10r of FIG. 2A). Nonetheless, tracking, storing, indicating, and transmitting of primary battery 14p parameters such as ERI and EOL are included in algorithm 250 for maximum informational benefit.

If Vbr eventually falls below Vbr+ (208), algorithm 250 preferably stores, indicates, and transmits for patient review the need for recharging using external charger 70 (216/218). However, so long as Vbr>Vbr− (212), use of the rechargeable battery 14r continues, repeating steps 208-218 as necessary.

As Vbr falls during its use, and assuming that the patient has failed to charge the rechargeable battery 14r, Vbr≤Vbr− (212), the primary battery 14p can be used (222) if Vbp>Vbp_EOL (220). ERI can again be assessed (252) and if issued, it and a forecasted EOL can be stored, indicated, and/or transmitted (254) (only once, and not if this occurred earlier at step 206). ERI assessment occurs at this point in algorithm 250 (compares steps 204, 206) to ensure that ERI is recognized when the primary battery 14p is being used. If forecasted earlier, EOL can be updated (224), again by extending the forecasted EOL in accordance with how long the rechargeable battery 14r had been used in its previous session.

If the rechargeable battery 14r has not been suitably recharged to Vbr+ (208), the primary battery 14p will continue to be used (steps 216/218, 212, 220, 222, 224). If eventually recharged to Vbr≥Vbr+ (208), it is then again used (210), with the process continuing to assess and update ERI, the need for recharging, and selection of the appropriate battery 14r or 14p for IPG 110 use depending on Vbr and Vbp.

When the primary battery 14p reaches EOL (220), only the rechargeable battery 14r can be used to power the IPG 110, although this is of lesser concern when the IPG 110's main battery is the rechargeable battery 14r. Steps 226-236 regarding use of the rechargeable battery 14r once the primary battery 14p is depleted can occur as described earlier with respect to algorithm 200 and FIG. 7A.

Figure 8B:
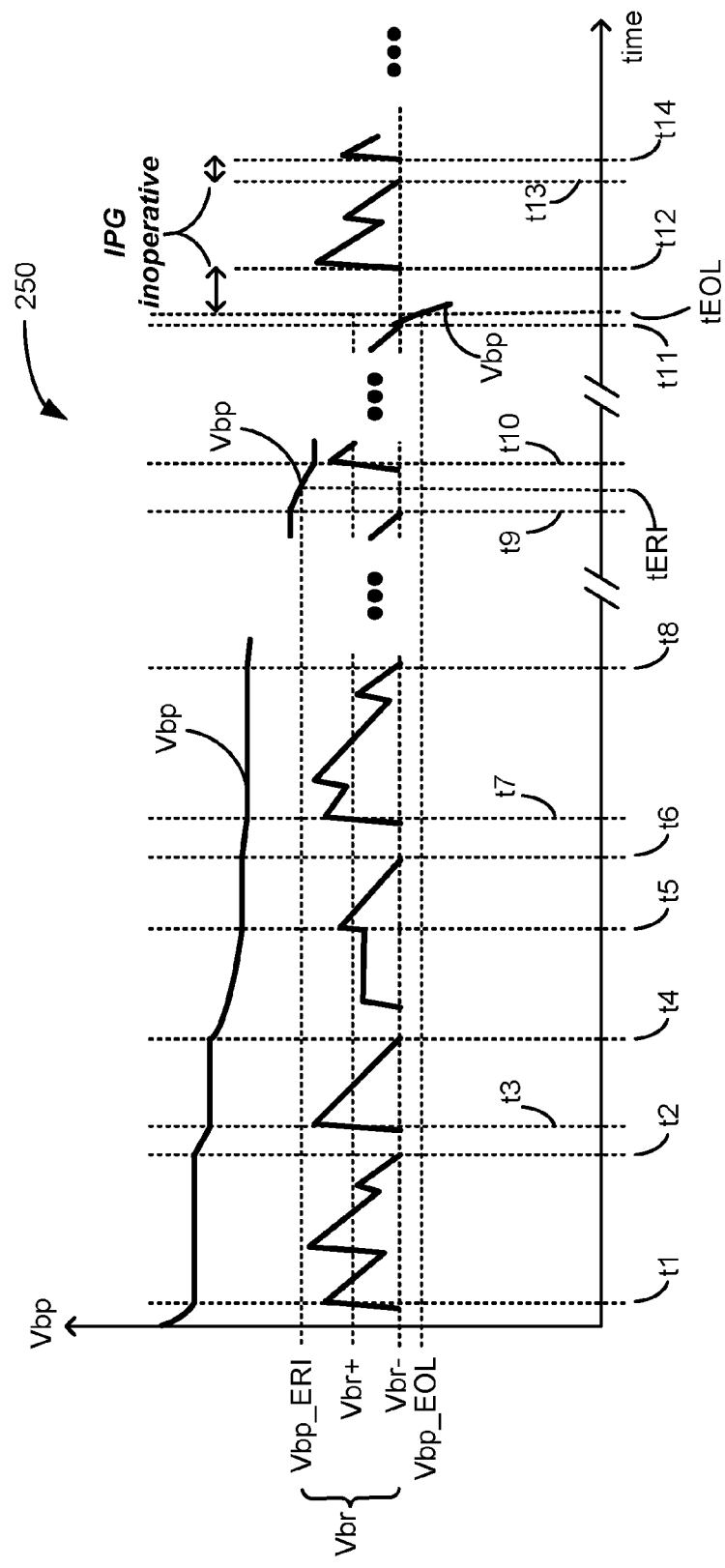
FIG. 8B shows the voltages of the rechargeable and primary batteries using the algorithm of FIG. 8A.

The effect of algorithm 250 on battery voltages Vbr and Vbp are shown in FIG. 8B, and should be understandable by the reader to this point based on earlier discussions. Note that algorithm 250, and use of IPG 110, still provides therapy by virtue of the back-up primary battery 14p, even during periods where the rechargeable battery 14r is not sufficiently charged (e.g., wherever Vbp falls and is being drawn upon: before t1; from t2 to t3; from t4 to t5; etc.). This again reduces circumstances in which the IPG patient would be without therapy, such as if the patient forget to charge his IPG 110, or is without his external charger 70 for an extended period of time.

Figure 1:
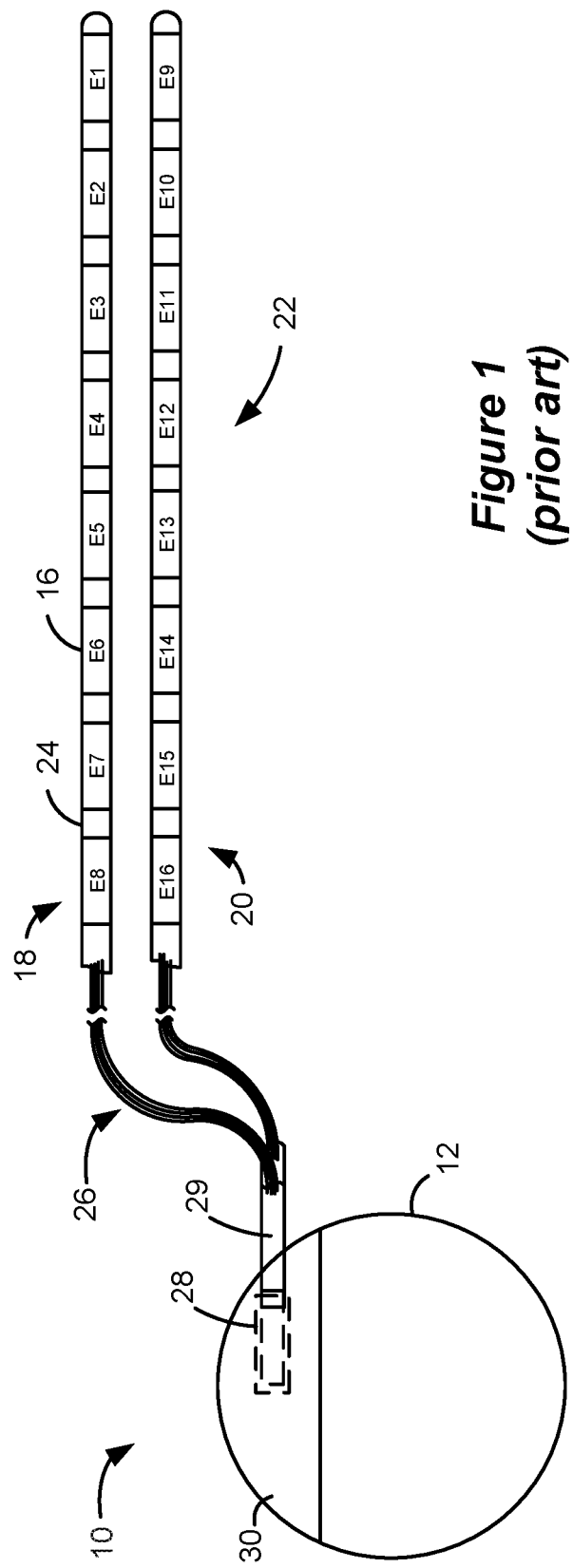
FIG. 1 shows an Implantable Pulse Generator (IPG) and the manner in which electrodes are affixed in accordance with the prior art.
Figure 3A:
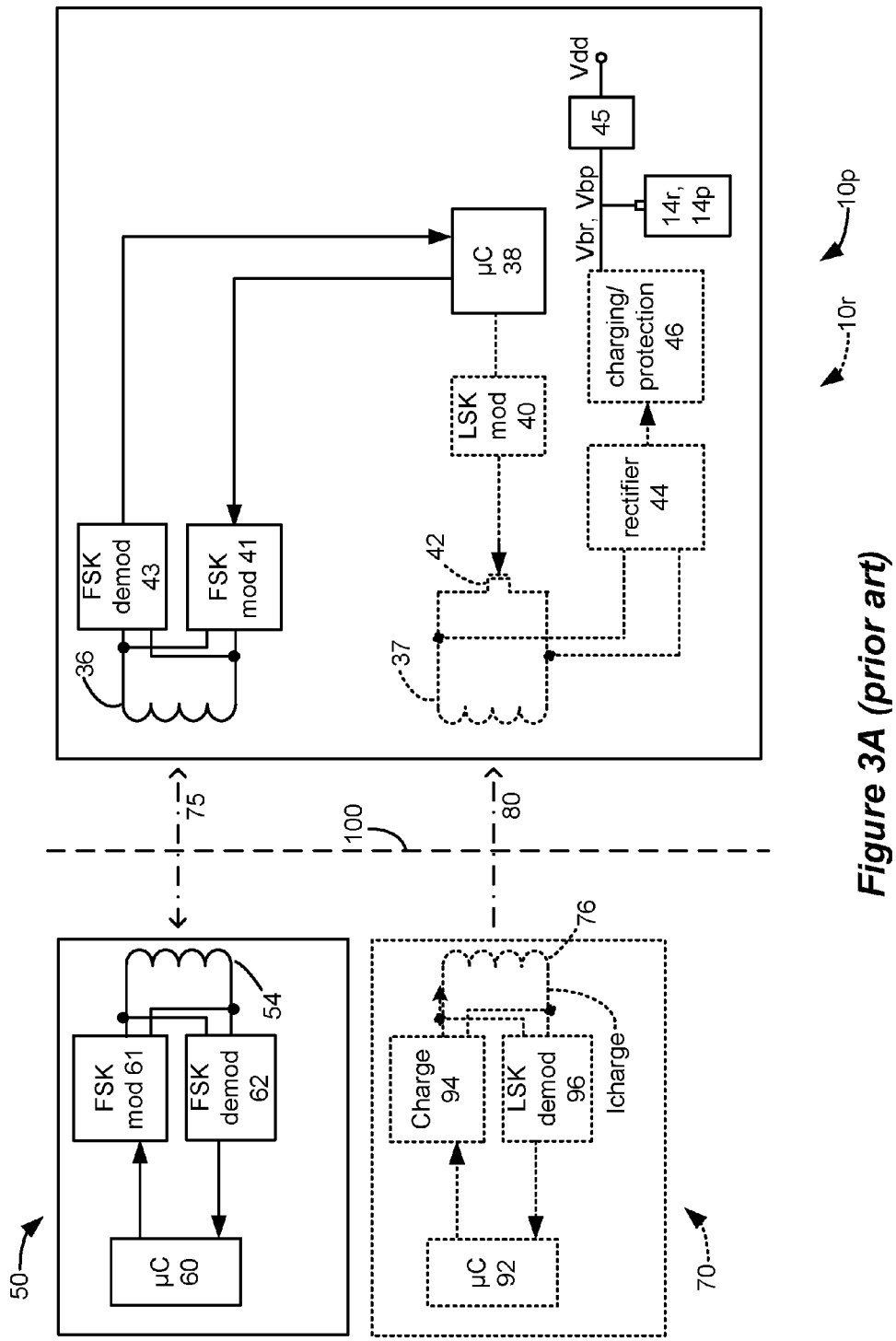
FIGS. 3A and 3B show circuitry in the external charger, the external controller, and in either of the rechargeable battery IPG or the primary battery IPG, in accordance with the prior art.
Figure 3B:
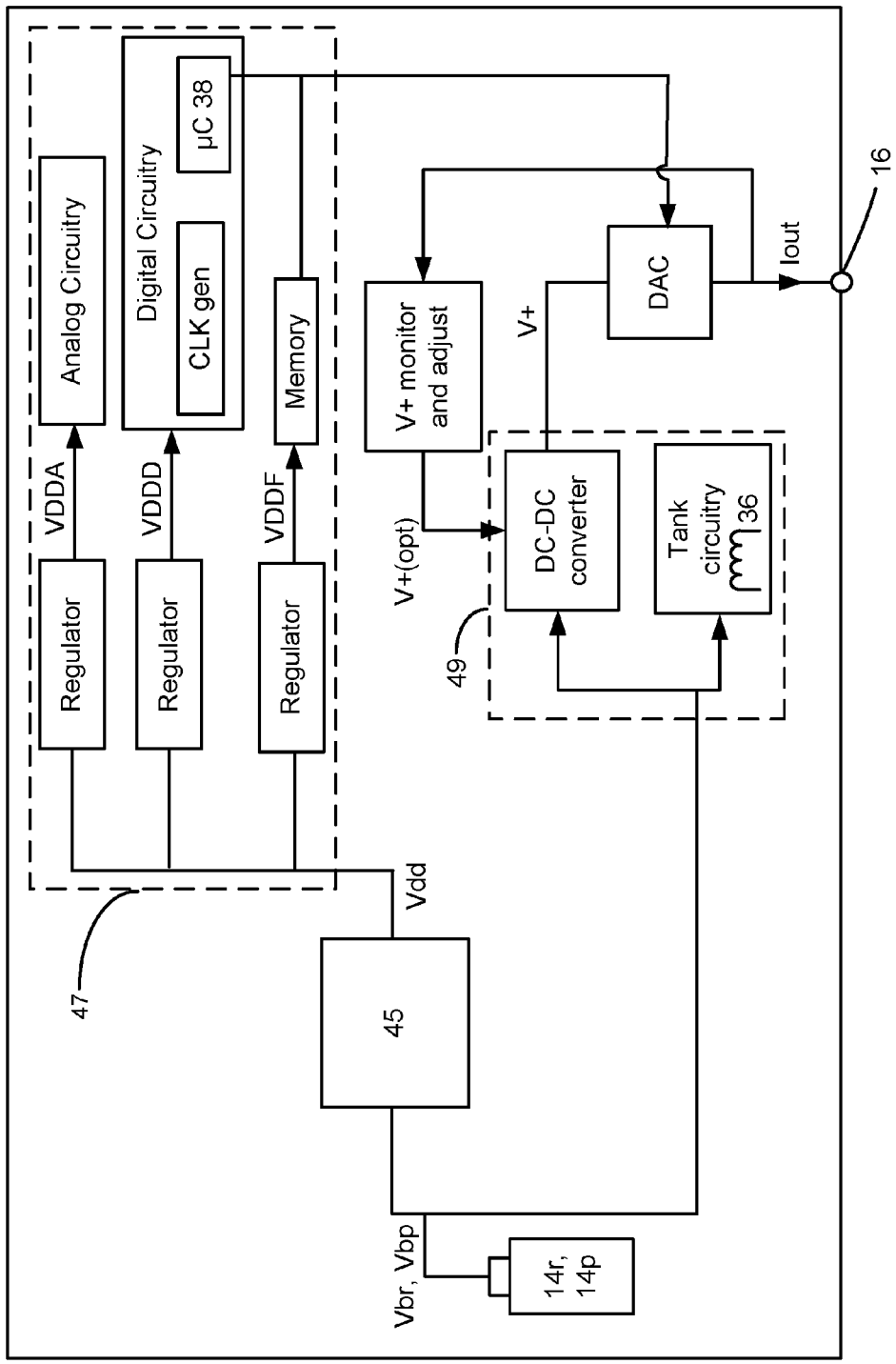
Figures 4A, 4B:
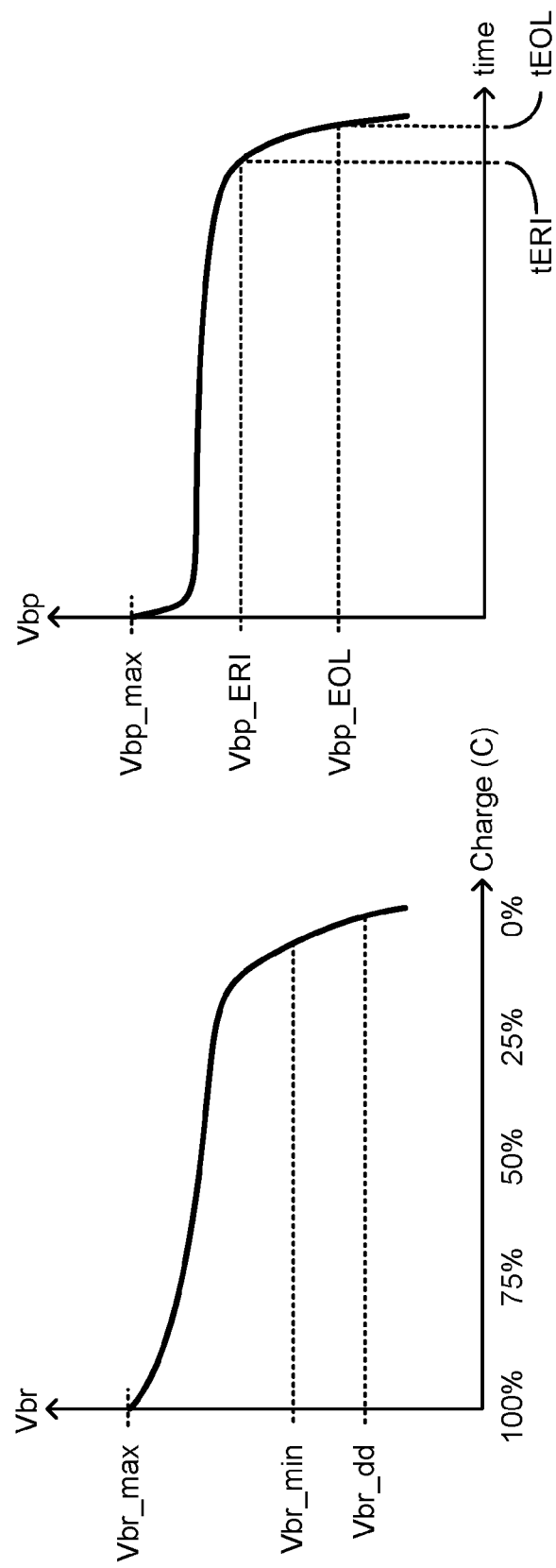
FIGS. 4A and 4B show curves illustrating rechargeable battery and primary battery depletion for the IPGs of FIGS. 2A and 2B.

Regardless whether dual-battery IPG 110 is configured and programmed to use algorithm 200 or 250, various battery data determined from use of the algorithms are preferably provided for patient review and action, as shown in FIG. 9. Such battery data can be provided to any external device that the patient uses to communicate with the IPG 110, such as the external controller 50 (FIG. 2D), in which case FSK telemetry might be used, or external charger 70 (FIG. 2C), in which case LSK telemetry might be used, as described earlier. In either case, the external devices 50 and 70 contain receiver circuitry for receiving the battery data, for example demodulators 62 and 96 respectively, as shown in FIG. 3A.

Use of the external controller 50 is preferred, as this device generally already comprises a graphical user interface suitable for displaying and interacting with such battery data. However, use of a traditional external controller is not strictly necessary. Although not shown, an external charger 70 may also comprise a graphical user interface, and thus battery data can also be telemetered to that device for review and interaction. Alternatively, a dual-purpose external device capable of controlling both therapy settings and battery charging can be used having a graphical user interface suitable for review of and interaction with telemetered battery data. Such a dual-purpose external device can be integrated into a single device housing, or may comprise connectable components. See, e.g., U.S. Pat. Nos. 8,498, 716, 8,335,569, and 8,463,392.

In the example of FIG. 9, the telemetered battery data has been received at an external controller 50 (FIG. 2D) and appears on its display 57, and in particular in an IPG battery menu comprising a user interface option selected earlier by the patient. Shown for patient review are: the battery currently being used by the IPG (300); the current voltages of rechargeable battery 14r (Vbr) and primary battery 14p (Vbp) (302); an indication that the rechargeable battery 14r needs recharging (e.g., using external charger 70) (304); the date (time) when ERI issued for the primary battery 14b (if yet) (306); the date when EOL is forecasted to issue for the primary battery 14b (assuming ERI has already issued) (308); and the date when EOL issued for the primary battery 14b (if yet) (310).

Many of these pieces of battery data displayed in FIG. 9 were procured during operation of the algorithm 200 or 250, such as recharging indication 304 (216, 218, 234), ERI indication (206, 254); forecasted EOL indication 308 (206, 254, 224), and EOL indication 310 (226). Other battery data, such as the current values for battery voltages Vbr and Vbp (302), can be periodically determined either by the algorithms 200 or 250 (not shown) throughout the life of the IPG 110, or outside use of the algorithms. For example, the control circuitry 38 in IPG 110 may periodically determine Vbr and Vbp, and store them in the battery data log 39 (FIG. 6A) in the IPG 110, along with other data procured by the algorithm. Which battery is currently being used (300) can comprise a single bit in the battery data log 39.

While these pieces of battery data are ultimately telemetered to the external controller 50 (or other external device), they cannot necessarily be telemetered as soon as they are determined. For example, if ERI issues for the primary battery 14p, the IPG 110 may attempt to immediately telemeter that data to the external controller 50, but if the external controller 50 is not within range of the IPG 110, no communication session can occur. Accordingly, the pieces of battery data are preferably stored in battery data log 39 as described earlier, and telemetered to the external controller 50 at an appropriate opportunity. For example, if the IPG 110 receives an indication from the external controller 50 that it wishes to communicate, the IPG 110 may transmit an acknowledgement, followed by the data in battery data log 39. Or the IPG 110 may request to transmit the log 39, doing so only after the external controller 50 permits this to occur. The external controller 50 may also institute telemetry of the battery data by requesting the IPG 110 to send such data at the beginning of a communication session, or at other times during a communication session, such as when the patient selects the IPG battery menu displayed in FIG. 9.

It should be noted that battery data received at the external controller 50 can be displayed as is, or can be further processed at the external controller 50 to provide and display an indication of that telemetered battery data. For example, while the IPG 110 may telemeter a bit indicating whether recharging is needed, the IPG 110 may also telemeter the rechargeable battery voltage Vbr, leaving it to the external controller 50 to determine indicate whether recharging is needed (304)—that is, the external controller 50 can compare Vbr as telemetered to Vbr+. In another example, the IPG 110 may merely telemeter a time stamp at which EOL issued, leaving it to the external controller 50 to synchronize this time stamp and to determine a date for display understandable by the patient (310).

Also shown in FIG. 9 are one or more options 312r and 312p to allow the patient to select whether the rechargeable battery 14r or the primary battery 14p should be used in the IPG 110 at a given time. Preferably, these options 312 would not allow the patient to select a particular battery if it is depleted (e.g., if Vbr<Vbr−; Vbp<Vbp_EOL), although this is not strictly necessary. For example, the patient, knowing primary battery 14p has been depleted or is close to being depleted (per EOL indication 310 or EOL forecast 308), may still choose to use this battery 14p (312p), perhaps to save the rechargeable battery 14r for use at a later time when the patient believes IPG therapy will be more important. In another example, a patient having an IPG 110 with a main primary battery 14p and using algorithm 200 may choose to charge and use the rechargeable battery 14r (312r), even though ERI has not yet issued (306) and thus use of the rechargeable battery 14r is not yet indicated by algorithm 200. In other words, the patient could choose to extend the life of the main primary battery 14p in his IPG 110 in this manner.

Once a battery select option 312 is selected, transmitter circuitry (e.g., 61; FIG. 3A) can be used to transmit the patient's selection to the IPG 110 via the relevant communication link (e.g., 75). Selecting either option 312 would preferably disable use of the battery selection algorithm 200 or 250 in the IPG 110, at least temporarily if not permanently. Should the patient later desire to return to using the algorithm to choose an appropriate battery, the stop option 314 can be selected for this purpose, which when telemetered to and received by the IPG 110 can return the IPG 110 to use of the algorithm. Alternatively, returning to use of the algorithm can occur after a temporary time period. Although not shown, a time period or schedule for use of a particular battery 14r or 14p could also be input to the graphical user interface of FIG. 9, with the algorithm being used at other times. Alternatively, the disclosed algorithms don't have to be used at all with the dual-battery IPG 110, and instead, the patient can be free to choose which battery 14r or 14p will be used in his IPG 110 at all times (per 312r or 312p).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
   a primary battery;
   a rechargeable battery;
   first operative circuitry;
   a power supply node configured to provide power to the first operative circuitry in the implantable medical device; and
   a control circuitry,
   wherein the control circuitry is configured to
   (a) couple the primary battery to the power supply node, after which the control circuitry is configured to
   (b) determine when a voltage of the primary battery is at or below a first threshold, after which the control circuitry is configured to
   (c) determine when a voltage of the rechargeable battery is at or above a second threshold, and when this occurs couple the rechargeable battery to the power supply node and decouple the primary battery from the power supply node, after which the control circuitry is configured to
   (d) determine when the voltage of the rechargeable battery is at or below a third threshold lower than the second threshold, and when this occurs couple the primary battery to the power supply node and decouple the rechargeable battery from the power supply node.

2. The device of claim 1, further comprising a charging coil configured to receive a charging field for recharging the rechargeable battery.

3. The device of claim 1, wherein the first threshold corresponds to an Elective Replacement Indicator (EM) for the primary battery designed to issue a predetermined time before the primary battery reaches its End Of Life (EOL).

4. The device of claim 1, wherein the primary battery is configured to operate the first operative circuitry down to a minimum voltage of the primary battery, and wherein the first threshold is above the minimum voltage.

5. The device of claim 1, wherein the control circuitry is further configured in step (b) to perform one or more of (i) storing, (ii) indicating, or (iii) wirelessly transmitting, an indication that the voltage of the primary battery is at or below the first threshold.

6. The device of claim 5, wherein the control circuitry is further configured in step (b) to perform one or more of (i) storing, or (ii) wirelessly transmitting, an EOL forecast indication for the primary battery when the voltage of the primary battery is at or below the first threshold.

7. The device of claim 1, wherein the rechargeable battery is configured to be charged to a maximum voltage, and wherein the second threshold is below the maximum voltage.

8. The device of claim 1, wherein the control circuitry is further configured in step (c) to perform one or more of (i) storing, (ii) indicating, or (iii) wirelessly transmitting, an indication that the rechargeable battery requires charging when the voltage of the rechargeable battery is below the second threshold.

9. The device of claim 1, wherein the rechargeable battery is configured to operate the first operative circuitry down to a minimum voltage of the rechargeable battery, and wherein the third threshold is above the minimum voltage.

10. The device of claim 1,
wherein the control circuitry is further configured in step (b) to perform one or more of (i) storing, or (ii) wirelessly transmitting, an EOL forecast indication for the primary battery when the voltage of the primary battery is at or below the first threshold, and
wherein the control circuitry is further configured in step (d) to update the EOL forecast indication, and to perform one or more of (i) storing, or (ii) wirelessly transmitting, the updated EOL forecast indication.

11. The device of claim 1, wherein after step (d) the control circuitry is further configured to
(e) determine when the voltage of the rechargeable battery is at or above the second threshold, and when this occurs couple the rechargeable battery to the power supply node and decouple the primary battery from the power supply node.

12. The device of claim 1, wherein the first operative circuitry comprises digital circuitry including the control circuitry.

13. The device of claim 12, wherein the first operative circuitry further comprises analog circuitry.

14. The device of claim 13, further comprising an antenna and current generation circuitry configured to produce a stimulation current at at least one electrode, wherein the first operative circuitry comprises a resonant tank circuit including the antenna, and a converter configured to generate a power supply voltage for the current generation circuitry.

15. The device of claim 1, further comprising second operative circuitry, wherein only the primary battery or the rechargeable battery provides power to the second operative circuitry in the implantable medical device.

16. The device of claim 15, further comprising an antenna and current generation circuitry configured to produce a stimulation current at at least one electrode, wherein the second operative circuitry comprises a resonant tank circuit including the antenna, and a converter configured to generate a power supply voltage for the current generation circuitry.

17. An implantable medical device, comprising:
a primary battery;
a rechargeable battery;
first operative circuitry;
a power supply node configured to provide power to the first operative circuitry in the implantable medical device; and
a control circuitry,
wherein the control circuitry is configured to
(a) determine when a voltage of the rechargeable battery is at or above a second threshold lower than a maximum voltage to which the rechargeable battery is configured to be charged, and when this occurs couple the rechargeable battery to the power supply node, after which the control circuitry is configured to
(b) determine
when the voltage of the rechargeable battery is at or below a third threshold lower than the second threshold, and
when a voltage of the primary battery is above a fourth threshold, and when these occur, couple the primary battery to the power supply node and decouple the rechargeable battery from the power supply node, after which the control circuitry is configured to
(c) determine when the voltage of the rechargeable battery is at or above the second threshold, and when this occurs couple the rechargeable battery to the power supply node and decouple the primary battery from the power supply node.

18. An implantable medical device, comprising:
a primary battery;
a rechargeable battery;
first operative circuitry;
a power supply node configured to provide power to the first operative circuitry in the implantable medical device; and
a control circuitry,
wherein the control circuitry is configured to
(a) couple the primary battery to the power supply node, after which the control circuitry is configured to
(b) determine when a voltage of the primary battery is at or below a first threshold, after which the control circuitry is configured to
(c) determine when a voltage of the rechargeable battery is at or above a second threshold, and when this occurs couple the rechargeable battery to the power supply node and decouple the primary battery from the power supply node, after which the control circuitry is configured to
(d) determine
when the voltage of the rechargeable battery is at or below a third threshold lower than the second threshold, and
when the voltage of the primary battery is above a fourth threshold at or below which the primary battery cannot operate the first operative circuitry, wherein the fourth threshold is lower that the first threshold,
and when these occur couple the primary battery to the power supply node and decouple the rechargeable battery from the power supply node.

19. The device of claim 18, wherein the control circuitry is further configured in step (d) to perform one or more of (i) storing, (ii) indicating, or (iii) wirelessly transmitting, an EOL indication for the primary battery when the voltage of the primary battery is at or below the fourth threshold.

20. The device of claim 18, wherein after step (d) the control circuitry is further configured to
(e) determine
when the voltage of the primary battery is at or below the fourth threshold, and
when the voltage of the rechargeable battery is above the third threshold,
and when these occur couple the rechargeable battery to the power supply node and Decouple the primary battery from the power supply node.

* * * * *